(12) United States Patent
Aganyan et al.

(10) Patent No.: US 10,420,929 B2
(45) Date of Patent: Sep. 24, 2019

(54) SYSTEMS AND METHODS FOR ELECTROSTIMULATION THERAPY

(71) Applicant: Aganyan Inc., Van Nuys, CA (US)

(72) Inventors: Hakop Aganyan, Los Angeles, CA (US); Suren Manukyan, Los Angeles, CA (US); Vagarshak Pilossyan, Los Angeles, CA (US); Silvia Aganyan, Los Angeles, CA (US)

(73) Assignee: Aganyan Inc., Van Nuys, CA (US)

( * ) Notice: Subject to any disclaimer, the term of this patent is extended or adjusted under 35 U.S.C. 154(b) by 0 days.

(21) Appl. No.: 15/279,442

(22) Filed: Sep. 29, 2016

(65) Prior Publication Data

US 2018/0085569 A1  Mar. 29, 2018

(51) Int. Cl.
| A61N 1/04 | (2006.01) |
| A01G 7/04 | (2006.01) |
| A61N 1/36 | (2006.01) |
| A61H 39/08 | (2006.01) |
| A61H 39/00 | (2006.01) |
| A61N 1/05 | (2006.01) |

(52) U.S. Cl.
CPC .............. *A61N 1/0492* (2013.01); *A01G 7/04* (2013.01); *A61H 39/002* (2013.01); *A61H 39/086* (2013.01); *A61N 1/36014* (2013.01); *A61H 2201/0157* (2013.01); *A61H 2201/1638* (2013.01); *A61N 1/0484* (2013.01); *A61N 1/0502* (2013.01); *A61N 1/36017* (2013.01)

(58) Field of Classification Search
CPC .. A61N 1/0492; A61N 1/0484; A61N 1/0502; A61N 1/36014; A61N 1/36017; A61H 39/086; A01G 7/04

USPC ..................... 607/2, 105, 113, 116, 144, 133
See application file for complete search history.

(56) References Cited

U.S. PATENT DOCUMENTS

| 4,616,654 | A | * | 10/1986 | Bacchelli | ............. | A61N 1/0452 |
| | | | | | | 607/149 |
| 5,354,321 | A | * | 10/1994 | Berger | ................ | A61N 1/0452 |
| | | | | | | 607/115 |
| 5,868,744 | A | * | 2/1999 | Willmen | ................ | A61B 18/14 |
| | | | | | | 606/50 |
| 8,025,673 | B1 | * | 9/2011 | Lyapko | ................ | A61H 39/002 |
| | | | | | | 606/189 |
| 2005/0187580 | A1 | * | 8/2005 | Skiba | ..................... | A61N 1/303 |
| | | | | | | 607/2 |

(Continued)

*Primary Examiner* — Christopher Koharski
*Assistant Examiner* — Roland Dinga
(74) *Attorney, Agent, or Firm* — Georgiy L. Khayet (57) ABSTRACT

A system for electrostimulation therapy includes two or more electrodes of different metals or metal alloys. The electrodes can be optionally provided on a flexible non-conducting substrate with a binder, thereby acting as a bandage or patch. Alternatively, the electrodes can be in the form of a needle, such as acupuncture needle, bracelets, armbands, wristbands, necklaces, or jewelry pieces. A method for electrostimulation therapy includes the steps of attaching a first electrode to a user or soil of a plant at a first location and attaching at least one additional electrode to the user or the plant at other locations for a predetermined period. The electrodes are not connected to a voltage or current source. Because at least two electrodes are of different metals, they cause an electrical current to flow via at least a portion of the user or the soil of the plant.

12 Claims, 6 Drawing Sheets

(56) References Cited

U.S. PATENT DOCUMENTS

| | | | |
|---|---|---|---|
| 2011/0118655 A1* | 5/2011 | Fassih | A61N 1/205 604/20 |
| 2014/0114142 A1* | 4/2014 | Shaoulian | A61B 5/0404 600/301 |
| 2014/0277271 A1* | 9/2014 | Chan | A61N 1/36003 607/48 |

* cited by examiner

SYSTEMS AND METHODS FOR ELECTROSTIMULATION THERAPY

BACKGROUND

Technical Field

This disclosure generally relates to electrical stimulation therapy. More specifically, this disclosure relates to systems and methods for electrical stimulation therapy where electrical current is generated by metal electrodes without using any electrical devices such for a voltage source or a current source.

Description of Related Art

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section.

Electrical stimulation (also referred herein to as "electrostimulation") is a therapeutic treatment that applies electrical stimulation in treating muscle spasms and pain, which can also be used in rehabilitation and preventive medicine, providing post-exercise recovery, and so forth. Some electrical stimulation methods involve elicitation of muscle contraction by causing electrical impulses to go through a certain area of a user's body. Other electrical stimulation methods, such as electrophoresis, involve generating an electromagnetic field or applying a direct electrical current to cause body fluids or drugs to move within the user's body.

Known electrical stimulation methods are based on the usage of electrical medical devices for producing electrical currents for applying to the user for treatment purposes. These electrical medical devices are not only expensive, but also inconvenient to use, especially when the electrical stimulation therapy should be given to a user for a prolonged period. Thus, advancements in electrical stimulation are desired.

SUMMARY

This section is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

According to one aspect of the disclosure, there is provided a method for electrical stimulation therapy. The method comprises the step of attaching a first electrode to a user at a first location, where the first electrode is made substantially of a first metal or metal alloy; and the first electrode is not connected to any electrical device. The method further comprises the step of attaching a second electrode to the user at a second location, where the second electrode is made substantially of a second metal or metal alloy. The second electrode is not connected to any electrical device. The first metal or metal alloy differs from the second metal or metal alloy. The first electrode and the second electrode cause an electrical current to flow through at least a portion of the user.

According to another aspect of the disclosure, there is provided a method for electrical stimulation therapy. The method comprises the step of attaching a first electrode to a soil of a plant at a first location, where the first electrode is substantially made of a first metal or metal alloy; and the first electrode is not connected to any electrical device. The method further comprises the step of attaching a second electrode to the soil of the plant at a second location, where the second electrode is made substantially of a second metal or metal alloy. The second electrode is not connected to any electrical device. The first metal or metal alloy differs from the second metal or metal alloy. The first electrode and the second electrode cause an electrical current to flow through at least a portion of the user.

According to yet another aspect of the disclosure, there is provided a system for electrical stimulation therapy. The system comprises a first electrode made substantially of a first metal, where the first electrode is not connected to any electrical device, and where a second electrode is made substantially of a second metal not connected to any electrical device, and where the first metal differs from the second metal. When the first electrode and the second electrode are attached to a user or a soil of a plant, the first electrode and the second electrode cause an electrical current to flow through at least one portion of the user or the plant.

Additional objects, advantages, and novel features of the examples will be set forth in part in the description, which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

Embodiments are illustrated by way of example and not limitation in the figures of the accompanying drawings, in which like references indicate similar elements and in which.

DETAILED DESCRIPTION OF EXAMPLE EMBODIMENTS

The present teachings generally relate to systems and methods for electrical stimulation of any living object, including any tissue or fluid of a human, an animal, a plant, or any other natural object. The electrical stimulation is provided or caused by applying at least two electrodes to a live object or soil of a plant, where the electrodes are substantially of different metals or different metal alloys, and not connected to any electrical device such a voltage or current source.

Most of tissues in a living object (e.g., a human, animal, or plant) include various liquids, such as water, a solution of water, or other liquids infused with salts, minerals, solvents, or other elements. It was found that the liquids or tissue of living objects can serve as an electrolyte or an electrically conducting solution. The two or more electrodes, when in contact with the living object or its fluids, create a difference in potentials between the electrodes without using any electrical current or voltage sources. The difference in potentials causes electrons to flow in the living object from one of the electrodes to another, while holes/ions can flow in the living object in the opposite direction. In this sense, one of the electrode can be considered as a cathode, while another electrode can be considered as an anode. The difference in potentials can be created only when the electrodes are of different metals or metal alloys. According to the present teachings, the electrodes can produce a difference of electric potential in a range from about 0.1 volts to about 1.4 volts, while the electrical current flowing from one electrode to another can be in a range from about 0.1 microampere to about 1,400 microampere. These ranges of voltages and electrical currents appear to be safe for humans and most of the animals and plants.

The electrodes can be applied to or mounted on the living object or the soil of the pant at any distance therebetween (e.g., from one millimeter to two meters or even more) and still provide the difference in potentials. The inventors found that an electrical current will be caused by the electrodes when they are placed or attached to a living object at any distance therebetween. The electrostimulation therapy with the electrodes of this disclosure can be conveniently performed for long periods of time, ranging from about 1 hour to 24 hours or even more.

The methods for electrostimulation of this disclosure can be used to treat many disorders of people, animals, and other living objects, including plants. For example, the present methods for electrostimulation can be used to treat infections, viral disorders, bacterial disorders, and reduce pain. It was unexpectedly found that the methods for electrostimulation can deactivate viruses and bacteria without harming normal tissues. Thus, the methods for electrostimulation may treat or assist in treating Acquired ImmunoDeficiency Syndrome (AIDS) or Human ImmunoDeficiency Virus (HIV) disorders. The electrostimulation can be also helpful or assisting in treating some or all cancers. In addition, the inventors found that the present teachings can be helpful in treating the following human disorders or conditions: urinary incontinence, enlarged prostate, arthritis, back pain, diabetic ulcers, fibromyalgia, headaches, herpes, neck pain, neuropathy, sciatica, shingles, sports injuries, tendon and ligament pain, rheumatism, carpal tunnel syndrome, inflammatory arthritis, fighting infectious diseases, viral infections, migraines, capsulitis, synovitis, disc diseases, stroke, tendonitis, bursitis, intractable pain, torticollis, soft tissue, bell's palsy, surgical incision, abdominal cramps, edema, whiplash, postop healing, injury, myofascial pain, chronic pain, temporomandibular joint dysfunction, sinus problems, acute pain, decubitus, myositis, facial lifting, skin rejuvenation, hypertension, macular degeneration, major depression, essential tremor, micro current deep brain stimulation, obsessive-compulsive disorder, Parkinson's disease, Alzheimer's disease, and so forth. The present teachings can be also helpful in improving well-being, and providing physiotherapy, anti-aging, and cosmetic treatments, among others.

Notably, the present teachings do not require usage of any additional electrolytic solution or conductive gel to be placed between the electrodes and the living object. No reservoirs with a reducing agent and no reservoirs with an oxidizing agent are needed between the electrodes and the living object according to embodiments of this disclosure. Moreover, the present teachings of electrostimulation should not be used and should not be applied directly on wounds.

The inventors of the present methods for electrostimulation suggest the following explanation of why these methods help in treating disorders and improving general well-being of living objects. Each tissue type in a body of a human and many animals has its own signature electrical frequency, which may be disrupted by an injury or a disease. The electrostimulation therapy according to the embodiments of this disclosure restores normal frequencies within human cells, resulting in remarkable improvements in treating pain, inflammation, and restoring a function of the cells. At the cellular level, the electrostimulation therapy stimulates a dramatic increase in adenosine triphosphate (ATP), the energy that fuels all biochemical functions in a human body. It also bumps up protein synthesis, which is necessary for tissue repair. The ensuing enhancement in blood flow and decrease in inflammation translates into reductions in pain and muscle spasms, as well as increased range of motion.

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

For purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

Additionally, all ranges provided herein include the upper and lower values of the range unless explicitly noted. For example, the term "about" shall mean a reasonable deviation of a value accompanying this term. If it is not specified otherwise, the term "about" may refer to a variation of 20% from an indicated value. In the case of a range of values, the term "about" may refer to a 20% variation from both the lower and upper limits of the range.

Moreover, it shall be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," and so forth). Spatially relative terms, such as "beneath," "below," "lower," "above," "upper" and the like may be used to describe an element or feature's relationship to another element(s) and/or feature(s) as, for example, illustrated in the drawings. It shall be appreciated the spatially relative terms are intended to encompass different orientations of system for electrostimulation or its elements in use in addition to the orientation depicted in the figures. For example, if the system for electrostimulation or any of its components in the drawings is turned over, elements described as "below" and/or "beneath" other elements or features would then be oriented "above" the other elements or features. The system for electrostimulation or its components may be otherwise oriented (e.g., rotated 90 degrees or at other orientations) and the spatially relative descriptors used herein interpreted accordingly.

The term "user" shall be construed to mean any individual, human, animal, or any other living object, using the system for electrostimulation according to any embodiment described herein. The term "user" shall also encompass a patient, client, customer, and the like. In some embodiments, the term "user" can be construed to mean a plant.

The term "electrostimulation" shall be construed to mean a process for creating, producing, applying, or providing an electrical current in any tissue or liquid of any living object such as a human, animal, or plant. The terms "electrostimulation" and "electrical stimulation" can be used interchangeably.

The term "electrode" shall be construed to mean any electric conductor of any shape or design. The electrode can be made of a metal or metal alloy. Each of the electrodes can be made as a single whole, although other implementations are also possible and within the scope of this disclosure. In certain embodiments of this disclosure, the electrodes have one or more homogeneous (solid, smooth) surfaces without any substantial irregularities.

Now, exemplary embodiments are described with reference to the drawings. The drawings are schematic illustrations of idealized example embodiments. As such, variations from the shapes of the illustrations as a result, for example, of manufacturing techniques or tolerances, are to be expected. Thus, example embodiments discussed herein should not be construed as limited to the particular shapes of regions illustrated herein but are to include deviations in shapes that result, for example, from manufacturing.

Figure 1:
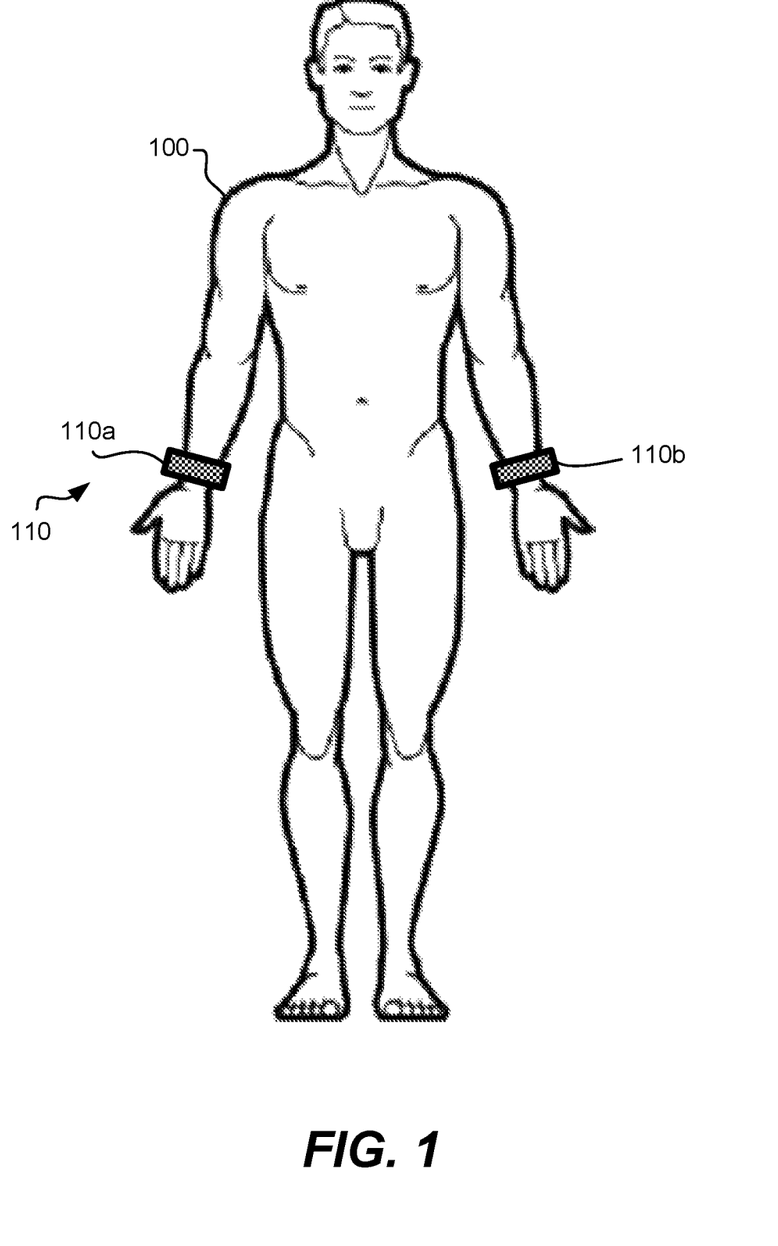
FIG. 1 shows a front view of a user wearing a system for electrostimulation according to one example embodiment.

FIG. 1 shows a front view of a user 100 wearing a system 110 for electrostimulation according to one example embodiment. The system 110 for electrostimulation includes two or more electrodes, where at least one of the electrodes is made of a metal or metal alloy that is different from other electrodes. In this example, the system 110 for electrostimulation includes two electrodes 110a and 110b, where the electrode 110a is made substantially of one metal, while the electrode 110b is made substantially of another metal. The metals for the electrodes of the system 110 can be selected from a wide range of different metals, including, for example, aluminum (Al), gold (Au), iron (Fe), copper (Cu), zinc (Zn), palladium (Pa), magnesium (Mg), platinum (Pl), silver (Ag), titanium (Ti), tungsten (W), and any alloys thereof. The electrodes 110a and 110b can also be made of various alloys containing chromium (Cr) that are used to make stainless steel. Thus, stainless steel (of any grade) can be used to make electrodes. In other words, the disclosed technology can utilize potential difference between various metals as well as various metal alloys. As discussed above, when the electrodes 110a and 110b are of different metals (or metal alloys), they produce a difference of electric potential in a range from about 0.1 volts to about 1.4 volts, while the electrical current flowing from one electrode to another can be in a range from about 1 microampere to about 1,400 microampere. The following table provides approximate differences of electric potential that are produced by different metal pairs:

TABLE 1

| First Electrode 110a | Second Electrode 110b | Voltage (difference of potential), approximate values, error can be up to 20% |
| --- | --- | --- |
| Al | Au | 0.7 volt |
| Au | Fe | 0.04 volt |
| Al | Fe | 0.6 volt |
| Au | Cu | 0.01 volt |
| Cu | Fe | 0.06 volt |
| Au | Zn | 0.85 volt |
| Zn | Fe | 0.9 volt |
| Zn | Cu | 0.8 volt |
| Zn | Al | 0.2 volt |
| Al | Pd | 0.65 volt |
| Au | Pd | Less than 0.01 volt |
| Cu | Pd | 0.12 volt |
| Fe | Pd | 0.04 volt |
| Zn | Pd | 0.8 volt |
| Al | Ag | 0.65 volt |
| Au | Ag | 0.01 volt |
| PD | Ag | 0.01 volt |
| Cu | Ag | 0.15 volt |
| Fe | Ag | 0.02 volt |
| Zn | Ag | 0.85 volt |
| Al | Pl | 0.6 volt |
| Pl | Pd | Less than 0.01 volt |
| Pl | Au | Less than 0.01 volt |
| Pl | Ag | Less than 0.01 volt |
| Cu | Pl | 0.08 volt |
| Fe | Pl | 0.01 volt |
| Zn | Pl | 0.7 volt |
| Mg | Zn | 0.65 volt |
| Mg | Fe | 1.3 volt |
| Mg | Cu | 1.1 volt |
| Mg | Al | 0.7 volt |
| Mg | Pl | 1.2 volt |
| Mg | Au | 1.4 volt |
| Mg | Pd | 1.2 volt |
| Mg | Ag | 1.2 volt |

Table 1 is applicable to all embodiments of this disclosure. Some example metal pairs for the electrodes 110a, 110b can be as follows. When the first electrode 110a is substantially of silver and the second electrode 110b is substantially of zinc, the difference of potential can be about 850 millivolts when the electrodes 110a, 110b are applied to a human body. When the first electrode 110a is substantially of iron and the second electrode 110b is substantially of zinc, the difference of potential can be about 900 millivolts when the electrodes 110a, 110b are applied to a human body. The electrical current between the electrodes 110a, 110b can vary and be in a range from about 1 microampere to about 1,400 microampere. It is important to mention that the electrodes 110a, 110b are not electrically or operatively connected to any medical device, including a voltage source or a current source. In some embodiments, however, the electrodes 110a, 110b can be electrically connected with one another to make a closed circuit (e.g., through any living tissue).

Referring back to FIG. 1, the electrodes 110a, 110b can be made in the form of a wearable item such as a bracelet, wristband, armband, leg band, necklace, or any piece of jewelry. The electrodes 110a, 110b can be placed, fixed, attached, secured, or provided at any location of the human body, animal, plant, or soil of the plant. For example, as shown in FIG. 1, the first electrode 110a being in the form of a first bracelet, is provided on the right wrist of the user 100, and the second electrode 110b being in the form of a second bracelet, is provided on the left wrist of the user 100.

The electrodes 110a, 110b can be provided in other forms too. For example, the electrodes can be attached to or provided by a skin patch, adhesive bandage, spray metal paint, topical, transdermal, intradermal, subcutaneous, intramuscular, intravenous, or other forms. The electrodes 110a, 110b can be also of different designs or shapes. For example, the electrodes 110a, 110b can be in the form of needles, discs, plates, panels, metal meshes, nanowires, metal dots, and the like. The distance between the electrodes 110a, 110b can be in a range from 10 millimeters to 2 meters or even more. The dimensions of the electrodes 110a, 110b can vary in any reasonable range. For example, the surface area of the electrodes 110a, 110b that are in contact with the user (or other living object) can be from about 1 square millimeter to about 200 square centimeter.

Figure 2:
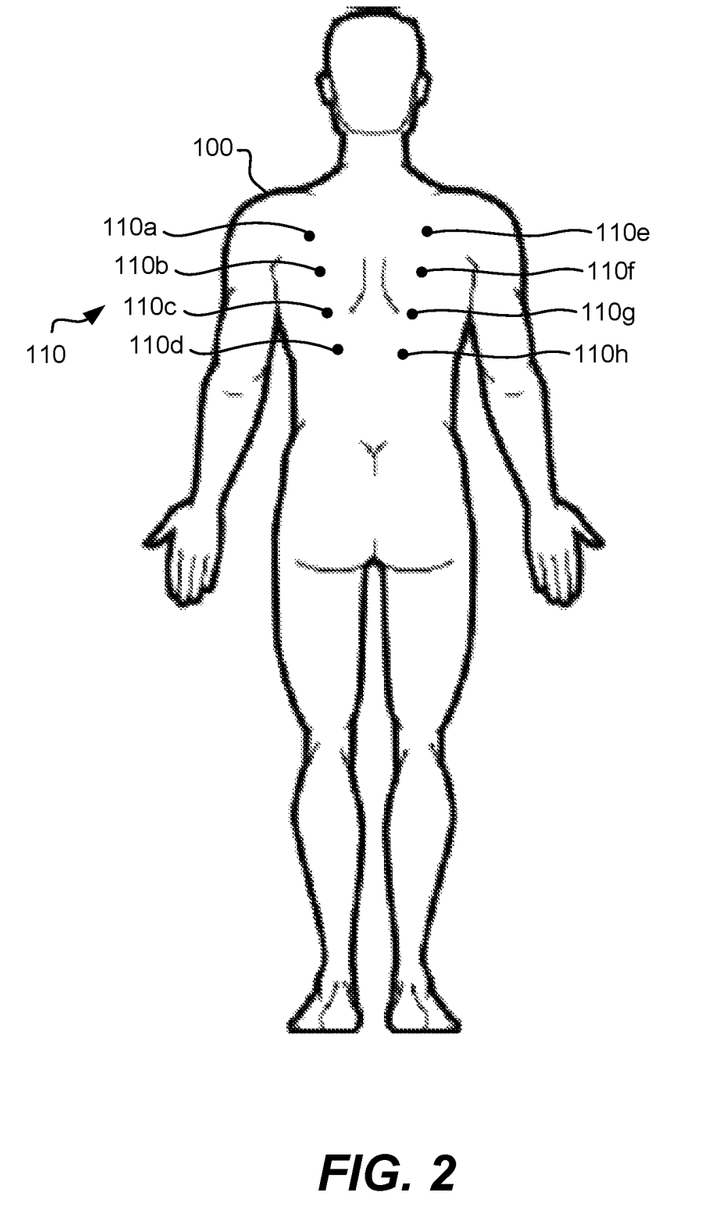
FIG. 2 shows a back view of a user using a system for electrostimulation according to another example embodiment.

FIG. 2 shows a back view of a user 100 using a system 110 for electrostimulation according to another example embodiment. Here, system 110 for electrostimulation includes a plurality of electrodes 110a, 110b, 110c, 110d, 110e, 110f, 110g, and 110h. The number of electrodes is not limited to eight (like in this embodiment) and, generally, can be two or more electrodes. In this embodiment, the electrodes 110a, 110b, 110c, 110d, 110e, 110f, 110g, and 110h are in the form of acupuncture needles that are inserted into the user's skin.

In one example, the electrode 110a is made of metal A, while other electrodes 110b-110h can be made of metal B. In another example, the electrodes 110a, 110b are made of metal A, while other electrodes 110c-110h can be made of metal B. In yet another example, the electrodes 110a, 110b, 110c are made of metal A, while other electrodes 110d-110h can be made of metal B. In yet another example, the electrodes 110a-110d are made of metal A, while other electrodes 110e-110h can be made of metal B. In yet another example, the electrodes 110a, 110c, 110e, 110g are made of metal A, while the electrodes 110b, 110d, 110f, 110h are made of metal B.

In other example embodiments, the electrodes 110a-110h can be made of more than two different metals. For example, the electrode 110a is made of metal A, the electrode 110b is made of metal B, while other electrodes 110c-110h are made of metal C. In another example, the electrode 110a is made of metal A, the electrode 110b is made of metal B, the electrode 110c is made of metal C, while other electrodes 110d-110h are made of metal D. Any other combinations can be also used, but their description is not given in this document.

Figure 3:
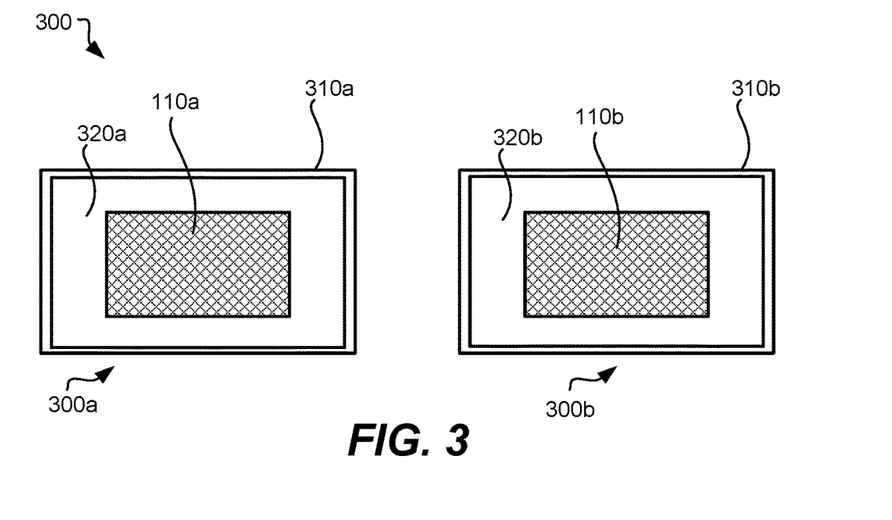
FIG. 3 shows a front view of a system for electrostimulation according to yet another example embodiment.

FIG. 3 shows a front view of a system 300 for electrostimulation according to yet another example embodiment. The system 300 for electrostimulation includes at least two separate wearable elements 300a and 300b. The wearable elements 300a and 300b can refer to a patch or a bandage. The wearable elements 300a, 300b include substrates 310a, 310b, respectively. The substrates 310a, 310b can be flexible substrates that are not electrically conductive. For example, each of the substrates 310a, 310b can include a pliable base, such as a medical grade 100% polyester fabric material; however, other materials can be also used such as gauze, mesh, fabric, polymer base, or other materials as long as they are pliable.

Each of the substrates 310a, 310b includes a binder 320a, 320b, respectively, for releasable binding to a surface or skin of a living object (e.g., a human or animal). The binder 320a, 320b can be made of non-electrically conductive material such as a polymer or any other suitable medium used in certain coating, laminating, or adhesion techniques.

Each of the substrates 310a, 310b also includes an electrode 110a, 110b, respectively. As discussed above, the electrodes 110a, 110b are of different metals or metal alloys. The electrodes 110a, 110b can be in the form of a metal plate, puck, disc, sphere, mesh, coating (e.g., a silver nanowire layer), film, layer, and the like.

In certain embodiments, the wearable elements 300a and 300b are removably attached to a surface or skin of living object at a distance ranging from about 10 millimeters to about 2 meters or even more. The wearable elements 300a, 300b can remain attached to the surface or skin of living object for a period of at least one minute or more. In certain embodiments, there can be provided additional wearable elements similar to the wearable elements 300a, 300b. The number of such wearable elements is not limited.

Figures 4, 5:
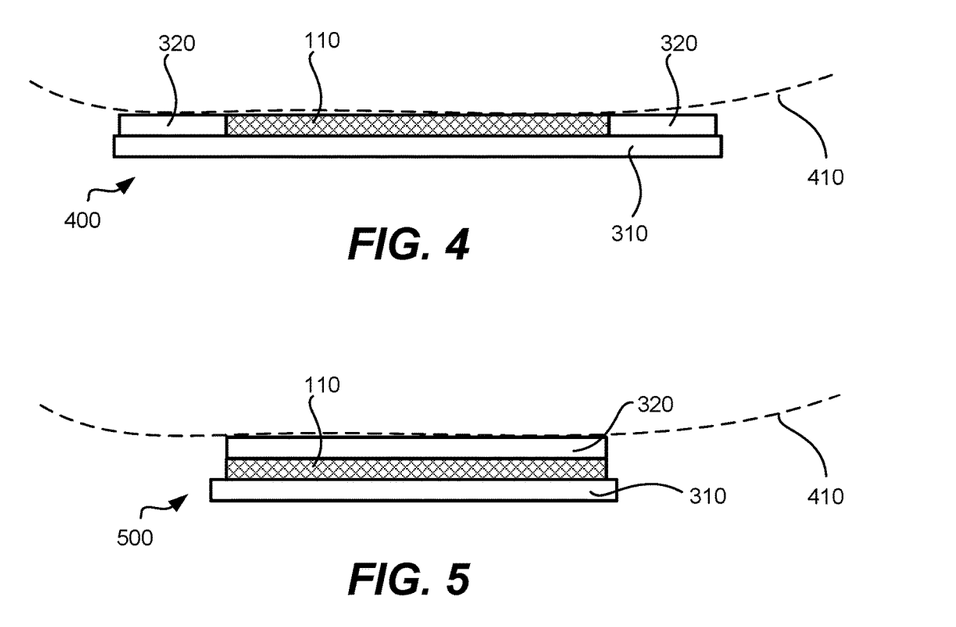
FIG. 4 shows a side view of a wearable element of a system for electrostimulation according to one example embodiment.
FIG. 5 shows a side view of a wearable element of a system for electrostimulation according to yet another example embodiment.

FIG. 4 shows a side view of a wearable element 400 of a system for electrostimulation according to one example embodiment. The wearable element 400 can be an instant of wearable element 300a or 330b shown in FIG. 3. The wearable element 400 includes a flexible substrate 310, a binder 320 in the form of polymeric adhesive layer, and an electrode 110. The electrode 110 is secured on a surface of the flexible substrate 310. The binder 320 is provided on the same surface of the flexible substrate 310 substantially around the electrode 110. When the wearable element 400 is in contact with a surface or skin 410 of a living object, the binder 320 provides adhesive connection of the entire wearable element 400 for a long period of time such that the electrode 110 directly contacts the surface or skin 410 of the living object.

FIG. 5 shows a side view of a wearable element 500 of a system for electrostimulation according to yet another example embodiment. The wearable element 500 can be an instant of wearable element 300a or 330b shown in FIG. 3. The wearable element 500 includes a flexible substrate 310, a binder 320, for example, in the form of a polymeric adhesive layer, and an electrode 110. The binder 320 can exhibit electroconducting properties only when 320 is made of a non-conductive absorbing material and soaked in an electrolyte. In some example embodiments, the electrolyte can be substituted by tap water (rich with minerals).

The bottom surface of electrode 110 is secured on the top surface of the flexible substrate 310. The bottom of the binder 320 is provided on the top surface of the electrode 110 and optionally on the top surface of the flexible substrate 310 where there is no electrode 110. When the wearable element 500 is in contact with the surface or skin 410 of the living object, the binder 320 provides adhesive connection of the entire wearable element 500 such that the electrode 110 indirectly contacts the surface or skin 410 of the living object.

Figure 6:
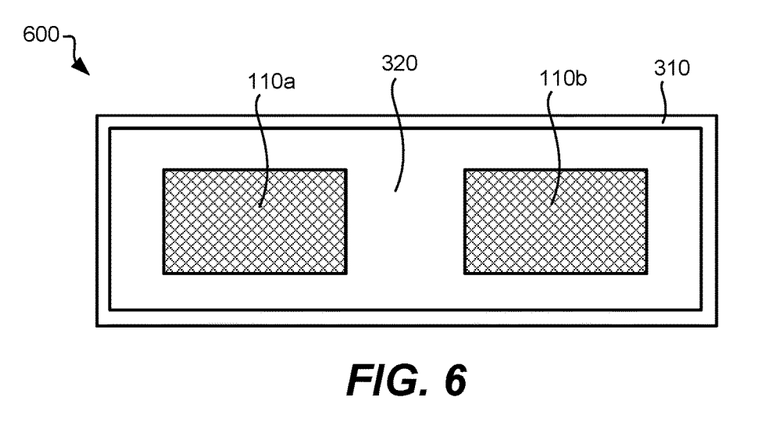
FIG. 6 shows a front view of a system for electrostimulation according to yet another example embodiment.

FIG. 6 shows a front view of a system 600 for electrostimulation according to yet another example embodiment. Generally, the system 600 for electrostimulation can be a single wearable element such as a patch or a bandage. The system 600 includes a substrate 310, which can be of a non-electrically conductive, but flexible material. For example, the substrate 310 can include a pliable base, such as a medical grade 100% polyester fabric material; however, other materials can be also used such as gauze, mesh, fabric, polymer base, or other materials as long as they are pliable.

The substrate 310 includes a binder 320 for releasable binding the entire system 600 to a surface or skin of a living object (e.g., a human, or animal). The binder 320 can be made of non-electrically conductive material such as a polymer or any other suitable medium used in certain coating, laminating, or adhesion techniques. The substrate 310 also includes two or more electrodes such as electrodes 110a, 110b. As discussed above, the electrodes 110a, 110b are of different metals or metal alloys. The electrodes 110a, 110b can be in the form of a metal plate, puck, disc, sphere, mesh, coating (e.g., a silver nanowire layer), film, layer, and the like.

Figure 7:
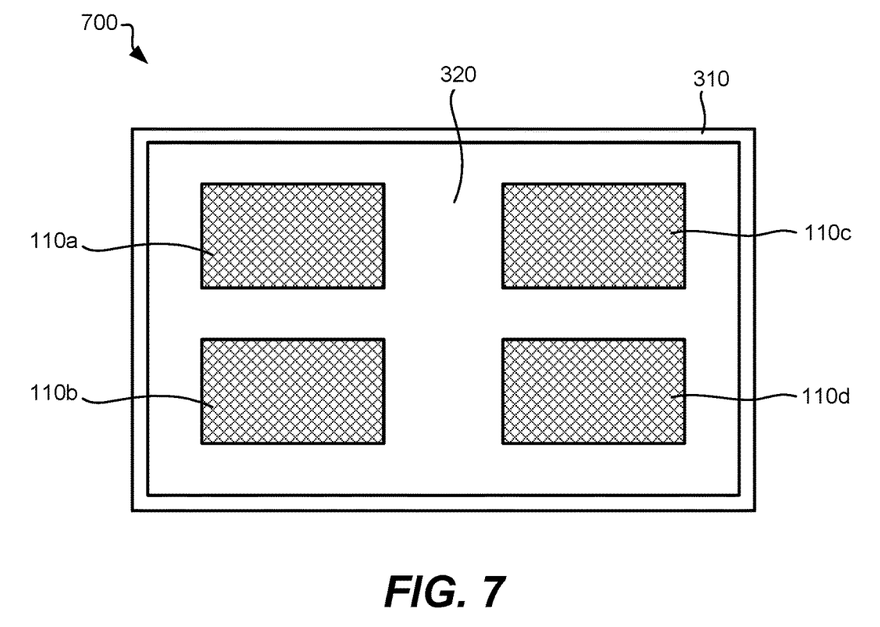
FIG. 7 shows a front view of a system for electrostimulation according to yet another example embodiment.

FIG. 7 shows a front view of a system 700 for electrostimulation according to yet another example embodiment. The system 700 for electrostimulation can be directed to a single wearable element such as a patch or a bandage. The system 700 includes a substrate 310, which can be of a non-electrically conductive, but flexible material. For example, the substrate 310 can include a pliable base, such as a medical grade 100% polyester fabric material; however, other materials can be also used such as gauze, mesh, fabric, polymer base, or other materials as long as they are pliable.

The substrate 310 includes a binder 320 for releasable binding the entire system 700 to a surface or skin of a living object (e.g., a human, or animal). The binder 320 can be made of non-electrically conductive material such as a polymer or any other suitable medium used in certain coating, laminating, or adhesion techniques. The substrate 310 also includes four or more electrodes such as electrodes 110a, 110b, 110c, and 110d. The electrodes 110a, 110b, 110c, and 110d can be in the form of a metal plate, puck, disc, sphere, mesh, coating (e.g., a silver nanowire layer), film, layer, and the like. As discussed above, the electrodes 110a, 110b, 110c, and 110d are of at least two different metals or metal alloys. For example, the electrode 110a is made of metal A, and the electrodes 110b, 110c, 110d are made of metal B. In another example, the electrode 110b is made of metal A, and the electrodes 110a, 110c, 110d are made of metal B. In yet another example, the electrode 110c is made of metal A, and the electrodes 110a, 110b, 110d are made of metal B. In yet another example, the electrode 110d is made of metal A, and the electrodes 110a, 110b, 110c are made of metal B. In yet another example, the electrodes 110a and 110b are made of metal A, and the electrodes 110c and 110d are made of metal B. In yet another example, the electrodes 110a and 110c are made of metal A, and the electrodes 110b and 110d are made of metal B. In yet another example, the electrode 110a is made of metal A, the electrode 110b is made of metal B, and the electrodes 110c and 110d are made of metal C. In yet another example, the electrode 110a is made of metal A, the electrode 110b is made of metal B, the electrode 110c is made of metal C, and the electrode 110d is made of metal D. Each of the metals A, B, C, and D can be selected from a group, comprising, for example, the following metals: aluminum (Al), gold (Au), iron (Fe), copper (Cu), zinc (Zn), palladium (Pa), magnesium (Mg), platinum (Pl), silver (Ag), and any alloy thereof.

Figure 8:
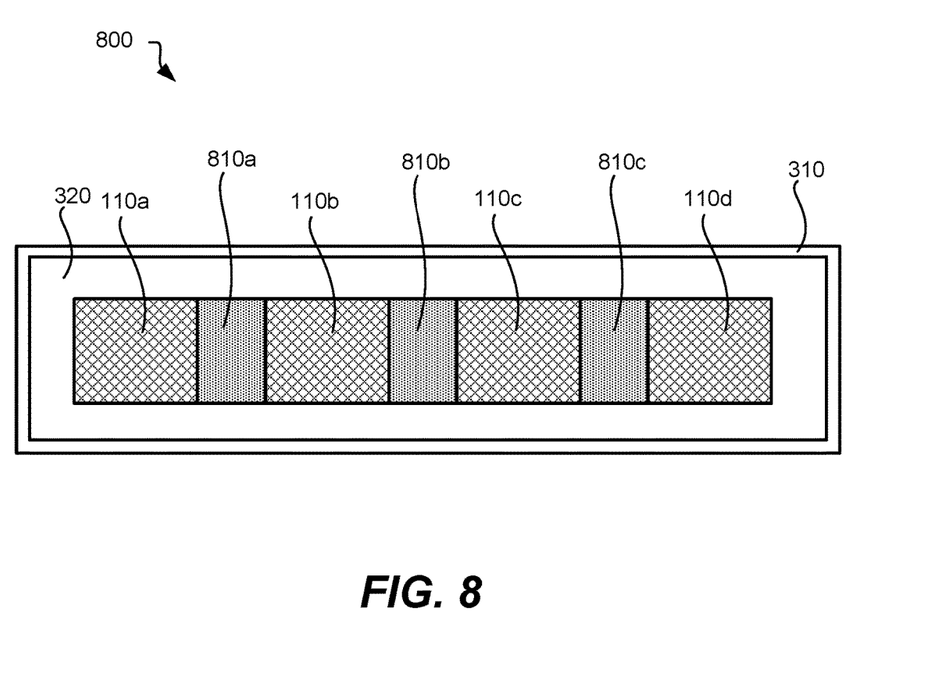
FIG. 8 shows a front view of a system for electrostimulation according to yet another example embodiment.

FIG. 8 shows a front view of a system 800 for electrostimulation according to yet another example embodiment. The system 800 for electrostimulation can be directed to a single wearable element such as a patch or a bandage. The system 800 includes a substrate 310, which can be of a non-electrically conductive, but flexible material. For example, the substrate 310 can include a pliable base, such as a medical grade 100% polyester fabric material; however, other materials can be also used such as gauze, mesh, fabric, polymer base, or other materials as long as they are pliable.

The substrate 310 includes a binder 320 for releasable binding the entire system 800 to a surface or skin of a living object (e.g., a human or animal). The binder 320 can be made of non-electrically conductive material such as a polymer or any other suitable medium used in certain coating, laminating, or adhesion techniques.

The substrate 310 also includes four or more electrodes such as electrodes 110a, 110b, 110c, and 110d. The electrodes 110a, 110b, 110c, and 110d can be in the form of a metal plate, puck, disc, spheres, semi-spheres, mesh, coating (e.g., a silver nanowire layer), film, layer, and the like. As discussed above, the electrodes 110a, 110b, 110c, and 110d are made up of two different metals or different metal alloys. For example, the electrode 110a is made of metal A, and the electrode 110b is made of metal B, the electrode 110c is made of metal A, and the electrode 110d is made of metal B. Each of the metals of the electrodes 110a, 110b, 110c, and 110d can be selected from a group, comprising, for example, the following metals: aluminum (Al), gold (Au), iron (Fe), copper (Cu), zinc (Zn), palladium (Pa), magnesium (Mg), platinum (Pl), silver (Ag), and so forth. When electrodes 110a, 110b, 110c, and 110d are arranged in series, the output voltage for electrostimulation therapy can be increased up to a desired value, provided there can be any other suitable number of electrodes 110a, 110b, 110c, and 110d.

Still referring to FIG. 8, there can be provided electrolyte layers 810a, 810b, 810c between the electrodes 110a-110d, respectively, as shown in the figure. The electrolyte layers 810a-810c can be of any suitable non-conductive absorbing materials. The embodiment shown in FIG. 8 illustrates how the difference of potentials created by the electrodes can be increased up to several voltages; however, in order for the system 800 to operate efficiently, the two end electrodes 110a and 110d must be placed, arranged, fixed, or attached onto the skin of the user: human or animal. The rest of the elements of system 800, in particular, the electrolyte layer 810a, the electrode 110b, the electrolyte layer 810b, the electrode 110c, and the electrolyte layer 810c should not meet the skin of the user. The electrodes 110a-110d are electrically interconnected in series using the electrolyte layers 810a-810c. In this case, the output voltage of the system 800 will be equal to a sum of the voltages generated by pairs of the electrodes 110a-110b, 110b-110c, and 110c-110d.

Figure 9:
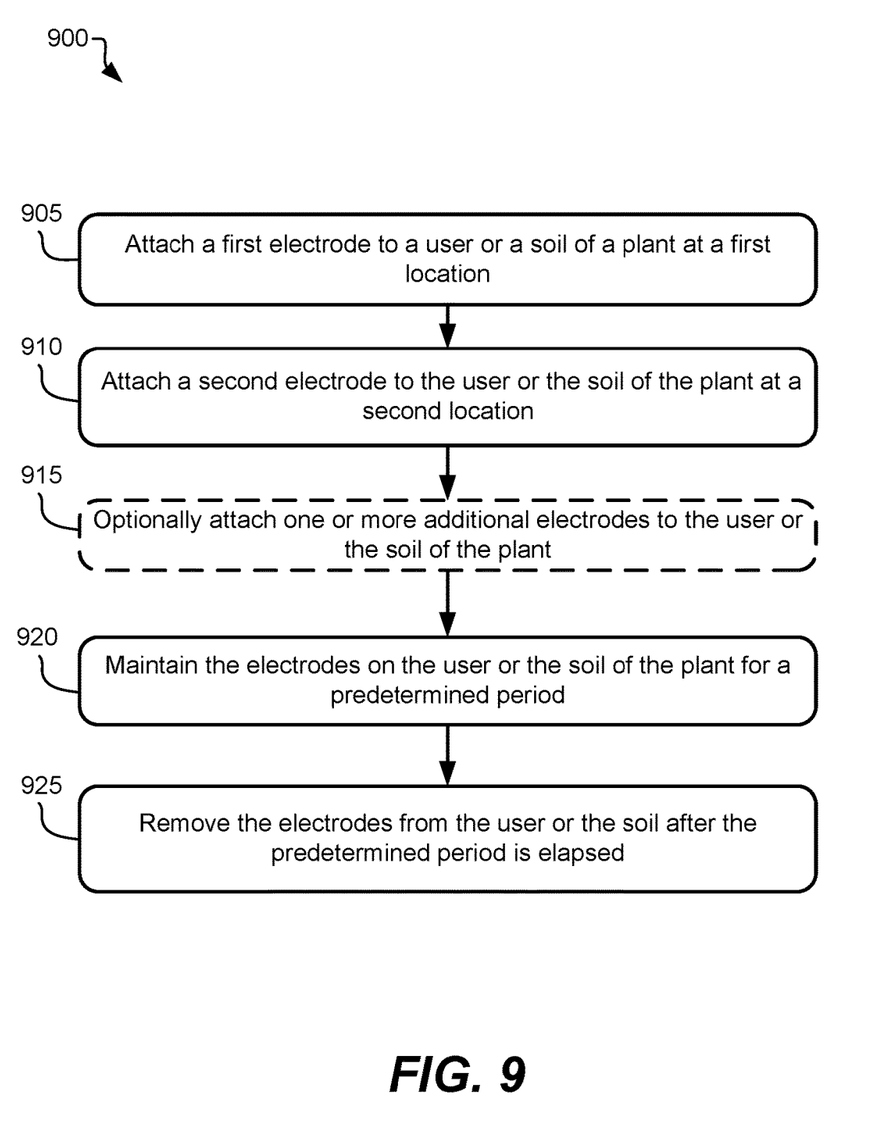
FIG. 9 is a process flow diagram showing a method for electrostimulation according to an example embodiment.

FIG. 9 is a process flow diagram showing a method 900 for electrostimulation according to an example embodiment. The method 900 may have additional steps not shown herein, but which can be evident for those skilled in the art from the present disclosure. The method 900 may also have fewer steps than outlined below.

At step 905, a first electrode 110a is attached, fixed, inserted, or provided to a user (human or animal) or soil of a plant at a first location. For these ends, a first wearable element can be provided that includes the first electrode 110a. The first wearable element can be placed, arranged, fixed, attached, or otherwise provided to the user or plant such that the first electrode 110a is in contact with a tissue or liquid of the user or plant. In some embodiments, the first electrode 110a can be inserted into skin of the user (e.g., when the electrodes are in the form of a needle). In some embodiments, the first electrode 110a can be inserted into a blood vessel, vein, or arteria of the user in the form of a needle to provide electrostimulation therapy of blood or other fluids.

At step 910, a second electrode 110b is attached, fixed, inserted, or provided to the user (human or animal) or the soil of the plant at a second location. For these ends, a second wearable element can be provided that includes the second electrode 110b. The second wearable element can be placed, arranged, fixed, attached, or otherwise provided to the user or soil of the plant such that the second electrode 110b is in contact with a tissue or liquid of the user or the soil of the plant. In some embodiments, the second electrode 110b can be inserted into skin of the user in the form of a needle. In some embodiments, the second electrode 110b can be inserted into a blood vessel, vein, or arteria of the user in the form of a needle to provide electrostimulation therapy of blood or other fluids. The first wearable element includes one of the following: a first bracelet, a first armband, a first leg band, and a necklace; however, the second wearable element can include one of the following: a second bracelet, a second armband, and a second leg band. The wearable elements can also refer to pieces of jewelry.

It should be noted, however, that in other embodiments, wearable elements are not necessary. For example, each of the first electrode 110a and the second electrode 110b is included in an acupuncture needle. Thus, the operation of attachment of the first electrode to the user or the soil of the plant can include inserting the first electrode 110a through skin of the user or inserting in the soil of the plant; similarly, the operation of attachment of the second electrode 110b to the user or the soil of the plant includes inserting the second electrode 110b through skin of the user.

As discussed above, the first electrode 110a is substantially of a first metal, while the second electrode 110b is substantially of a second metal, which differs from the first metal. Moreover, none of the electrodes is connected to any electrical device. In addition, the first location differs from the second location. After the first electrode and the second electrode are in contact with the user or the soil of the plant, they cause an electrical current to flow via at least a portion of the user or the soil of the plant.

At optional step 915, one or more additional electrodes (similar to electrodes 110a, 110b) can be attached, fixed, inserted, or provided to the user (human or animal) or the soil of the plant at additional locations. Similar to above, one or more additional wearable elements can be provided such that any of the additional electrodes is in contact with the tissue or liquid of the user or the soil of the plant. In some embodiments, the additional electrodes can be inserted into skin of the user or inserted into a blood vessel, vein, or arteria of the user to provide electrostimulation therapy of blood or other fluids.

At step 920, the first electrode 110a, the second electrode 110b, and all other additional electrodes (if any) are maintained at their locations of the user or the soil of the plant for a predetermined period. The predetermined period can be in a range from about 1 hour to about 24 hours or more, during which electrostimulation therapy is provided. The electrostimulation therapy involves generation of the electrical current by the electrodes 110a, 110b, etc. in a range from about 0.1 microampere to about 1,400 microampere.

At step 925, the first electrode 110a, the second electrode 110b, and all other additional electrodes (if any) are removed from the user or the soil of the plant after the predetermined period is elapsed. As discussed above, the method 900 for electrostimulation can treat various disorders or conditions of people, animals, and improve growth of the plants.

Thus, the systems and methods for electrostimulation have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A method for electrical stimulation therapy, the method comprising:
    positioning a first electrode at a first location over a body of a user, wherein the first electrode is substantially of a first metal or a first metal alloy, and wherein the first electrode is not connected to any electrical device or an electrical power source;
    wearing the first electrode on the body of the patient as a first wearable element, wherein the first wearable element includes one of the following: a first bracelet, a first armband, a first leg band, and a necklace;
    positioning a second electrode at a second location over the body of the user, wherein the second electrode is substantially of a second metal or a second metal alloy, wherein the second electrode is not connected to any electrical device or an electrical power source, wherein the first metal or the first metal alloy differs from the second metal or the second metal alloy, wherein the first location differs from the second location, and wherein the first electrode and the second electrode are configured to be positioned contactlessly with respect to each other and cause an electrical current to flow via at least a portion of the user; and
    wearing the second electrode on the body of the patient as a second wearable element, wherein the second wearable element includes one of the following: a second bracelet, a second armband, and a second leg band, the second wearable element being positioned on the body separately from the first wearable element, wherein:
        a distance between the first electrode and the second electrode is from 1 centimeter to 2 meters;
        a surface area of the first electrode is from about 1 square millimeter to about 200 square centimeters; and
        a surface area of the second electrode is from about 1 square millimeter to about 200 square centimeters.

2. The method of claim 1, wherein the first location is a wrist of the user, and wherein the second location is another wrist of the user.

3. The method of claim 1, wherein each of the first electrode and the second electrode is included in an acupuncture needle, wherein the configuring of the first electrode to be positioned over the body of the user includes configuring the first electrode to be inserted through skin of the user, and wherein the configuring of the second electrode to be positioned over the body of the user includes configuring the second electrode to be inserted through skin of the user.

4. The method of claim 1, wherein the first electrode is provided on a first flexible substrate, wherein the second electrode is provided on a second flexible substrate, and wherein each of the first flexible substrate and the second flexible substrate includes a binder for binding each of the first flexible substrate and the second flexible substrate to skin of the user such that the first electrode and the second electrode contact the skin of the user.

5. The method of claim 1, wherein the first electrode is provided on a flexible substrate, wherein the second electrode is provided on the flexible substrate, and wherein the flexible substrate includes a binder for binding the flexible substrate to skin of the user such that the first electrode and the second electrode contact the skin of the user.

6. The method of claim 1, wherein the electrical current is in a range from about 0.1 microampere to about 1,400 microampere.

7. The method of claim 1, wherein the first electrode and the second electrode provide a difference of electric potential in a range from about 0.1 volts to about 1.4 volts.

8. The method of claim 1, further comprising:
maintaining the first electrode at the first location of the user for a predetermined period;
maintaining the second electrode at the second location of the user for the predetermined period, wherein the predetermined period is at least 1 hour; and
removing the first electrode and the second electrode from the user after the predetermined period is elapsed.

9. The method of claim 1, further comprising:
configuring a third electrode to be positioned at a third location over the body of the user, wherein the third electrode is substantially of the first metal or the first metal alloy, and wherein the third electrode is not connected to any electrical device; and
configuring a fourth electrode to be positioned at a fourth location over the body of the user, wherein the fourth electrode is substantially of the second metal or the second metal alloy, wherein the fourth electrode is not connected to any electrical device, and wherein the first electrode, the second electrode, the third electrode, and the fourth electrode cause an electrical current to flow via at least one portion of the user.

10. The method of claim 9, wherein the first electrode is provided on a flexible substrate, wherein the second electrode is provided on the same flexible substrate, wherein the third electrode is provided on the same flexible substrate, wherein the fourth electrode is provided on the flexible substrate, and wherein the flexible substrate includes a binder for binding the flexible substrate to skin of the user.

11. The method of claim 1, wherein each of the first electrode is included in a first piece of jewelry, and wherein the second electrodes is included in a second piece of jewelry.

12. The method of claim 1, wherein each of the first electrode and the second electrodes has a needle shape, wherein the configuring of the first electrode to be positioned over the body of the user includes configuring the first electrode to be inserted in a first vein of the user, and wherein the configuring of the second electrode to be positioned over the body of the user includes configuring the second electrode to be inserted in a second vein of the user.

* * * * *